(12) United States Patent
Dehmer (10) Patent No.: US 9,267,630 B2
(45) Date of Patent: Feb. 23, 2016

(54) FERRULE CHUCK WITH SURFACE MICRO-GRIP (71) Applicant: AGILENT TECHNOLOGIES, INC., Loveland, CO (US)

(72) Inventor: Bernhard Dehmer, Waldbronn (DE)

(73) Assignee: Agilent Technologies, Inc., Santa Clara, CA (US)

(*) Notice: Subject to any disclaimer, the term of this patent is extended or adjusted under 35 U.S.C. 154(b) by 299 days.

(21) Appl. No.: 13/735,415

(22) Filed: Jan. 7, 2013

(65) Prior Publication Data
US 2013/0199981 A1  Aug. 8, 2013

(51) Int. Cl.
| | |
|---|---|
| *B01D 15/10* | (2006.01) |
| *G01N 30/02* | (2006.01) |
| *F16L 33/22* | (2006.01) |
| *B01L 3/00* | (2006.01) |
| *G01N 30/60* | (2006.01) |
| *B01D 15/22* | (2006.01) |
| *F16L 19/075* | (2006.01) |

(52) U.S. Cl.
CPC ............ *F16L 33/225* (2013.01); *B01D 15/10* (2013.01); *B01D 15/22* (2013.01); *B01L 3/563* (2013.01); *B01L 3/565* (2013.01); *F16L 19/075* (2013.01); *G01N 30/6004* (2013.01); *G01N 30/6039* (2013.01); *B01L 2300/0838* (2013.01)

(58) Field of Classification Search
CPC ........ B01D 15/08; B01D 15/10; B01D 15/22; B01L 3/563; B01L 3/565; B01L 2300/0838; F16L 19/06; F16L 19/075; F16L 33/22; F16L 33/223; F16L 33/225; G01N 30/6004; G01N 30/6039; G01N 2030/027; G01N 2030/6004; G01N 2030/6013

USPC .......... 210/198.2, 541, 542; 73/61.55, 61.56; 285/212, 339, 341–343, 353, 357, 285/382.1, 382.2; 422/70, 501, 527, 544, 422/546, 568
See application file for complete search history.

(56) References Cited

U.S. PATENT DOCUMENTS

| | | | | |
|---|---|---|---|---|
| 4,529,230 | A   * | 7/1985 | Fatula, Jr. ..................... | 285/341 |
| 7,338,088 | B2 * | 3/2008 | Salven et al. ................ | 285/124.3 |
| 7,553,455 | B1 * | 6/2009 | Renzi et al. ................... | 422/546 |
| 7,681,926 | B2 * | 3/2010 | Valaskovic et al. ........... | 285/342 |
| 7,900,976 | B2 * | 3/2011 | Kainec ........................... | 285/343 |

(Continued)

FOREIGN PATENT DOCUMENTS

| | | |
|---|---|---|
| WO | WO0116517 | 3/2001 |
| WO | WO0204939 | 1/2002 |

(Continued)

OTHER PUBLICATIONS

Office Action mailed Apr. 3, 2014 in EP Application No. 13150431.8-1554.

(Continued)

*Primary Examiner* — Joseph Drodge (57) ABSTRACT

A fitting for coupling a capillary to another component of a fluidic device is disclosed. The fitting includes a ferrule configured for enclosing a front part of the capillary and for contributing to a fluidic sealing between the fitting and the other component; a ferrule chuck configured for enclosing a back part of the capillary; and a housing configured for accommodating at least a part of the ferrule chuck and for pushing the ferrule chuck against the ferrule.

34 Claims, 2 Drawing Sheets

(56) References Cited

U.S. PATENT DOCUMENTS

| | | | |
|---|---|---|---|
| 7,909,367 B2* | 3/2011 | Plant et al. | 285/249 |
| 8,201,854 B2* | 6/2012 | Ford et al. | 285/385 |
| 2004/0017981 A1* | 1/2004 | Jovanovich et al. | 385/68 |
| 2006/0113794 A1* | 6/2006 | Plant et al. | 285/339 |
| 2007/0241556 A1* | 10/2007 | Smahl | 285/272.1 |
| 2008/0164694 A1 | 7/2008 | Zdroik et al. | |
| 2009/0295156 A1 | 12/2009 | Ford et al. | |
| 2010/0133806 A1* | 6/2010 | Barnett et al. | 285/24 |
| 2011/0025047 A1 | 2/2011 | Zelechonok et al. | |
| 2012/0169040 A1* | 7/2012 | Barnett et al. | 285/24 |
| 2013/0298647 A1* | 11/2013 | Falk-Jordan | 73/61.55 |
| 2014/0152003 A1* | 6/2014 | Michienzi | 285/375 |
| 2014/0375048 A1* | 12/2014 | Van Pelt | 285/31 |

FOREIGN PATENT DOCUMENTS

| | | |
|---|---|---|
| WO | 03036103 | 5/2003 |
| WO | WO2011076244 | 6/2011 |

OTHER PUBLICATIONS

Office Action mailed Sep. 18, 2015 in Chinese Patent Application No. 201310004542.1 (Unofficial/non-certified translation provided by foreign agent included).

* cited by examiner

FERRULE CHUCK WITH SURFACE MICRO-GRIP

CROSS-REFERENCE TO RELATED APPLICATIONS

The present application claims priority under 35 U.S.C. §119(e) from G.B. Patent Application No. 1202077.2 filed on Feb. 7, 2012 and assigned to the present assignee. The entire disclosure of G.B. Patent Application No. 1202077.2 is specifically incorporated herein by reference.

BACKGROUND

The present invention relates to a fitting for a fluidic device.

In liquid chromatography, a fluidic analyte may be pumped through a column comprising a material which is capable of separating different components of the fluidic analyte. Such a material, so-called beads which may comprise silica gel, may be filled into a column tube which may be connected to other elements (like a control unit, containers including sample and/or buffers). During operation, such columns may be subjected to high pressures of, for instance, up to 600 bar and more.

Fittings for coupling different components, such as separation columns and conduits, of fluidic devices are commercially available and are offered, for instance, by the company Swagelok (see for instance http://www.swagelok.com).

A known fitting element is configured to provide a fluidic coupling to a fluidic device, and comprises a capillary and an inlay located in a cavity of a front side of the capillary. The inlay protrudes over the front side, at least before coupling of the capillary to the fluidic device. Upon coupling of the capillary to the fluidic device, the front side is fitted to the fluidic device for connecting a fluid path of the capillary to a fluid path of the fluidic device, and the inlay provides a sealing of the fluid path of the capillary and the fluidic device.

A known fitting assembly comprises a nut, a ferrule, and a ferrule tip that may be assembled by an operator. The fitting assembly includes a nut with first and second ends, with the second end configured to receive the first end of a ferrule, and a ferrule tip with a first end having an externally tapered portion configured to abut the second end of the ferrule and a second end configured to be received in a component or fitting of a liquid chromatography system. The nut, ferrule and ferrule tip of the fitting assembly have passageways therethrough for receiving and removably holding tubing.

Another known fitting includes an elongated cylindrical body with a conical ferrule secured to its forward end, and with the body and ferrule having aligned through bores sized to allow a capillary tube to be passed through them. The elongated body has medially located external helical threads, and a knurled nut is rotatably coupled to these threads. The body also has elongated axially directed gripping fingers with inwardly facing gripping regions thereon normally spaced from but suited to be biased radially against the capillary tube in the fitting bores. A tubular gripping nut is threaded onto the external body threads, suited to be axially shifted along the body upon relative nut/body rotation. The nut and body have cooperating cam surfaces suited to engage upon relative nut/body rotation and bias the finger gripping regions tightly against the capillary tube for securely retaining tube as positioned within the fitting.

However, the requirements regarding sealing performance and mechanical stability of a fitting of fluidic measurement devices further increases with further increasing operation pressure values.

What is needed, therefore, is a fitting for a fluidic device that overcomes at least the shortcomings of known apparatuses described above.

SUMMARY

According to a representative embodiment, a fitting (or a connector) for coupling a capillary (such as a tubing having an inner fluid lumen) to another component (for instance a chromatographic column) of a fluidic device (such as a liquid chromatography device) is provided, the fitting comprising a ferrule configured for enclosing a front part (wherein the term "front" may refer to an end of the fitting facing the other component) of the capillary and for contributing to a fluidic sealing between the fitting and the other component, a ferrule chuck configured for enclosing a back part (wherein the term "back" or "rear" may refer to an end of the fitting being located remote from the other component) of the capillary, a housing (such as a fitting nut) configured for accommodating at least a part of the ferrule chuck (and optionally of at least a part of the ferrule, wherein alternatively the ferrule may be attached to the ferrule chuck when the latter is extending outside of the housing) and optionally for pushing the ferrule chuck against the ferrule (and against the capillary), and a microstructure formed as multiple microprotrusions on at least a part of a surface of the ferrule chuck for generating a form fit (particularly by embossing a micropattern in a surface of the capillary) with the enclosed back part of the capillary over a contact area (such as a hollow cylindrical contact area which may be interrupted by one or more longitudinal slits) between the ferrule chuck and the capillary upon tightening the fitting at the other component.

According to another representative embodiment, a fluidic device for processing a fluidic sample is provided, the fluidic device comprising a capillary for conducting the fluidic sample, another component for processing the fluidic sample (wherein the other component may have a fluidic conduit, such as another capillary or a channel in a substrate), and a fitting having the above mentioned features for coupling the capillary to the other component (particularly for providing a fluid-tight sealing between the fluidic conduit and the capillary).

According to still another representative embodiment, a method of manufacturing a fitting for coupling a capillary to another component of a fluidic device is provided, wherein the method comprises providing a ferrule configured for enclosing a front part of the capillary and for contributing to a fluidic sealing between the fitting and the other component, providing a ferrule chuck configured for enclosing a back part of the capillary, accommodating at least a part of the ferrule chuck (and optionally at least a part of the ferrule) in a housing configured for pushing the ferrule chuck against the ferrule, and forming multiple microprotrusions as a microstructure on at least a part of a surface of the ferrule chuck for generating a form fit (such as a micro form fit, i.e. a form fit on a micrometer scale) with the enclosed back part of the capillary over a (for instance continuous) contact area between the ferrule chuck and the capillary (particularly by embossing a micropattern in a surface of the capillary by a pressure applied by the microstructure onto the capillary) upon tightening the fitting at the other component.

Representative embodiments foster a proper gripping between a capillary and a gripping member, i.e. a ferrule chuck, circumferentially enclosing the capillary, wherein a form closure type gripping interaction is exerted by microprotrusions extending from a surface of the ferrule chuck and penetrating into a surface of the capillary, thereby embossing an inverse pattern of microindentations into the gripped surface of the capillary. By forming a microstructure of protrusions or teeth having a dimension in the order of magnitude of micrometers on a gripping surface of the ferrule chuck, a proper gripping form closure is enabled while simultaneously preventing an undesired patterning of the capillary which would contravene reuse of the capillary again. In contrast to conventional approaches forming macroscopic rips in a capillary surface resulting in a fixedly defined relative orientation between capillary and fitting, the microstructure used in an embodiment of the invention provides for micro indentations along a circumference of the capillary which however do not result in the undesired effect that reusing the capillary and/or the ferrule with another ferrule and/or capillary deteriorates the free selectivity of a relative spatial relationship between capillary and fitting. In other words, the microscopic patterning applied by the ferrule chuck onto the capillary according to an embodiment of the invention still allows a user-defined relative positioning between fitting and capillary when being reused. Hence, a free selectivity of the relative positional relationship of these two components is advantageously maintained since macroscopic ribs are avoided which would predefine a mutual alignment between capillary and fitting upon being used again. Thus, the microstructure provides for a sufficiently pronounced gripping form fit by forming some kind of form closure between capillary and ferrule chuck. Hence, a form closure or form fit rather than a pure friction fit may connect the capillary to the ferrule chuck.

Upon connecting the fitting to the other component (for instance by forming a screwing connection or another connection of two cooperating joint elements), the housing will engage the ferrule chuck (particularly by a form closure of cooperating slanted portions of housing and ferrule chuck) and will press the ferrule chuck circumferentially around the capillary, so that the microstructure will emboss indentations into the capillary surface to promote gripping of the capillary. Simultaneously, the ferrule chuck will push the ferrule forwardly so as to form a sealed coupling between the capillary and a connected fluidic conduit (such as another capillary, a lumen, a recess or the like) of the other component. Therefore, specifically upon tightening the fitting at the other component will result in the exertion of a two-dimensional gripping form fit which is strong enough to fulfill the strict requirements of modern liquid chromatography applications involving fluid pressure of 2000 bar and more.

Next, further representative embodiments of the fitting will be explained. However, these embodiments also apply to the fluidic device and to the method.

In an embodiment, the microstructure comprises multiple microprotrusions protruding from a surface of the ferrule chuck. For example, more than 100 or more than 1000, more particularly at least 5000 or even more than 10000 microprotrusions may be arranged on the two-dimensional surface on which the capillary is gripped by the ferrule chuck. In an embodiment, the number of microprotrusions may be in the order of magnitude of 10000. In an embodiment, the number of microprotrusions may however be less than 100000, otherwise the applicable force might not be large enough for such a large number of microprotrusions to emboss into the capillary. For example, the gripping may be applied along a continuous longitudinal extension of the capillary in a range between 1 mm and 2 mm and over the entire circumference of the capillary in the radial direction. Although coverage of an uninterrupted (wherein one or more slits may be formed) surface area of the ferrule chuck with the microprotrusions in longitudinal and/or circumferential direction is preferred, it is also possible that one or more gaps in longitudinal direction (e.g. slots forming wings) and/or one or more circumferential sections in circumferential direction is or are free of the microprotrusions. Therefore, the gripping form fit should be applied over a sufficiently large surface area, thereby providing for a strong and reliable gripping.

In an embodiment, a height, a width and/or a length of at least approximately 10%, particularly of at least approximately 50%, more particularly of at least approximately 90%, of the microprotrusions has or have a dimension in a range between approximately 0.5 µm and approximately 100 µm, particularly in a range between approximately 1 µm and approximately 50 µm, more particularly in a range between approximately 5 µm and approximately 20 µm. These dimensions of the microprotrusions are appropriate for preventing formation of an indentation pattern on the capillary which would deteriorate the possibility of reuse of the capillary with another fitting without a predefined alignment between capillary and fitting.

In an embodiment, the microprotrusions are randomly distributed over the surface of the ferrule chuck. The term "randomly" particularly denotes a statistical distribution of the microprotrusions over the ferrule chuck without defined ordering scheme so that the arrangement is free of any repetitive pattern or order. By such a random distribution, it can be prevented that a regular grip pattern of protrusions is formed which might also define an undesired preferred alignment direction or preferred contact area between capillary and fitting which would contravene the goal of a free selectivity of the gripping position. In contrast to this, the irregular pattern of microprotrusions provided according to an representative embodiment of the invention allows a user to freely select a gripping position along the capillary and therefore provides for a reusable fitting/capillary system. Thus, a stable, robust and repeatedly tightenable connection between fitting and capillary is achieved. Preferably but not essentially, the random distribution of microprotrusions or teeth has very small teeth being distributed statistically to such a degree that no regular embossing or punch marking pattern is formed.

In an embodiment, at least a part of the microprotrusions has a dimension which differs from a corresponding dimension of at least a part of adjacent, particularly radially or longitudinally (or axially) adjacent, ones of the microprotrusions. In other words, height, length and/or width (particularly diameter) of adjacent microprotrusions may be different. With such a concept, even a geometrically regularly pattern of microstructures may be used if the varying dimension of the microprotrusions destroys full regularity of the pattern.

In an embodiment, for at least a part of the microprotrusions, a distance between a pair of adjacent ones of the microprotrusions differs from a distance between microprotrusions of other pairs of adjacent microprotrusions which other pairs are adjacent to the pair. In other words, distances from a certain microprotrusion to different neighbored microprotrusions may differ, thereby again preventing formation of a completely regular pattern.

In an embodiment, the microprotrusions are arranged over the surface of the ferrule chuck free of a repeat pattern. Such a repeat pattern may be a predictable rule or formula according to which the microprotrusions are arranged on the ferrule chuck surface. Lack of such a repeat pattern ensures a desired asymmetry of the microprotrusion arrangement.

Although an irregular arrangement of microprotrusions is preferred for maintaining freedom of positioning the capillary when reusing capillary and/or fitting, also a regular arrangement of microprotrusions may satisfy this requirement, particularly when the microprotrusions have a dimension of 10 µm or less.

In an embodiment, the microstructure is formed, particularly exclusively, on a circumferential inner surface (for instance a circular cylindrical surface which may be interrupted by one or more longitudinal slits) of the ferrule chuck along which the ferrule chuck circumferentially grips the capillary. Particularly, an outer surface of the ferrule chuck may be free of the microstructure. However, it is also possible that one or more other surface portions of the ferrule chuck are covered by the microstructure. For instance, a grip between ferrule and ferrule chuck may be improved by forming a corresponding microstructure at a surface of the ferrule chuck contacting the ferrule. Moreover, additionally or alternatively, at least a part of the surface of the ferrule (particularly a circumferential inner surface of the ferrule along which the ferrule circumferentially grips or contacts the capillary or the ferrule chuck) may be equipped with such a microstructure. However, at least the interior surface of the housing may be free of microprotrusions (for instance such a surface may be polished) so that a low frictional free rotation of the components in an interior of the housing (particularly ferrule chuck and ferrule) relative to the housing may be enabled.

In an embodiment, the ferrule chuck is made of a metal, particularly steel, more particularly stainless steel. Such a material has sufficient flexibility so as to provide for a pivoting and self-adapting positioning.

In an embodiment, the ferrule chuck is made of a material having a Rockwell hardness of at least approximately 35 HRC, particularly of at least approximately 44 HRC. Thus, a sufficiently hard ferrule chuck is provided which has on one hand spring-like properties and on the other hand is capable of withstanding the high forces acting at 2000 bar fluid pressure.

In an embodiment, the ferrule chuck has a tapering, particularly a conically tapering, back section, wherein the tapering back section abuts against a tapering surface of the housing. Such a tapering portion of the ferrule chuck may be the portion actually experiencing a force from a surrounding housing so as to radially grip the capillary. The portion of the conically tapering back section with the largest extension in radial direction may be located closer to the ferrule than a narrowest portion of the tapering back section. A connection section of the ferrule chuck may be connected directly to the tapering back section for connecting the latter to a radially narrower part of the ferrule chuck. Hence, the connection section may be tapering as well, however with a sign of the slope being inverse to that of the tapering back section. Hence, a locally maximum radial extension of the ferrule chuck may be positioned at an interface between the connection section and the tapering back section. The portion of the connection section with the smallest extension in radial direction may be located closer to the ferrule than a widest portion of the connection section.

In an embodiment, the tapering back section is configured for transmitting a force from the housing to the capillary for gripping it by a form fit.

In an embodiment, the microstructure is formed, particularly exclusively, on a circumferential inner surface of the ferrule chuck, particularly on a tapering back section thereof (optionally including a circumferential inner surface of at least a part of the connection section). Hence, the other (particularly the exterior or outer) surface portions of the ferrule chuck may be free of the microstructure. Alternatively, also one or more outer surface portions of the ferrule chuck, may be covered by microstructures, wherein a contact surface between ferrule chuck and housing shall remain free of microprotrusion (to promote sliding between these components during mounting or fastening the fitting).

In an embodiment, the ferrule chuck has an annular, particularly a flat annular, front surface, wherein the annular front surface abuts against an annular back surface of the ferrule. Such a ring-like surface portion of the ferrule chuck may be oriented perpendicularly to an extension direction of the capillary. It may serve as an abutment face providing for a proper force transmission from the ferrule chuck to the ferrule in a longitudinal direction (wherein also radial forces may be transmitted in a similar manner by the form closure to which the microprotrusions contribute).

The ferrule and the ferrule chuck may be adapted (for instance by ensuring a rigid coupling between them by providing microprotrusions at an interface between them) to interact so that no relative rotation between the ferrule and the ferrule chuck is enabled when the fitting is mounted. Particularly, the contact surface of the ferrule or the ferrule chuck at which the ferrule or the ferrule chuck contacts the ferrule chuck or the ferrule, respectively, may be provided with microprotrusions with the properties described above or may have any other provision for enhancing a grip (such as a coating providing for a friction fit or macroscopic protrusions providing for a form fit).

In another embodiment, the ferrule chuck has an annular, particularly a flat annular, front surface, wherein the annular front surface is separated from an annular back surface of the ferrule by a gripping element promoting a grip between the ferrule and the ferrule chuck. Thus, a gripping element sandwiched between the ferrule and the ferrule chuck may provide for an indirect form fit between the ferrule and the ferrule chuck.

In an embodiment, the ferrule chuck has a hollow cylindrical front section ending at the annular front surface. The hollow cylindrical front section may be configured as an undeformable support (i.e. being sufficiently robust so that it is not deformed under the forces acting when connecting the fitting to the other component). Particularly, the hollow cylindrical front section may have the largest wall thickness along the entire ferrule chuck. In other words, even upon applying the forces which act on the ferrule chuck when connecting the fitting to the other component, the hollow cylindrical front section with its significant mechanical robustness (for instance wall thickness and therefore bulkiness) may still act as a solid body which does not follow any deformation of the rest of the ferrule chuck and provides a sufficiently large contact area with the ferrule.

In an embodiment, the ferrule chuck has a hollow cylindrical extension section arranged between the hollow cylindrical front section and the tapering back section (or the above mentioned connection section). The hollow cylindrical extension section may have a smaller wall thickness than the hollow cylindrical front section (alternatively, the hollow cylindrical front section may have the same or even a smaller wall thickness as/than the hollow cylindrical extension section, but may be supplemented by a connecting element to a ferrule). The hollow cylindrical extension section may be configured as a spring-like member, i.e. acting as a spring when the fitting is joint to the other component. The hollow cylindrical extension section may be directly connected to the hollow cylindrical front section and may have a significantly lower wall thickness. Therefore, upon tightening the fitting to a counter piece, the hollow cylindrical extension section may act in a spring-like manner, i.e. may be deformed. It may further act to support OF promote self-release or opening of the ferrule chuck.

The hollow cylindrical extension section may have a wall thickness in a range between approximately 0.1 mm and approximately 0.6 mm, particularly in a range between approximately 0.15 mm and approximately 0.4 mm. For instance, a corresponding hollow cylindrical extension section may be made of steel, particularly of stainless steel. In an embodiment, the wall thickness may be 0.2 mm. By the use of a sufficiently hard material and a spring-like tubular section of the above dimensions, the ferrule chuck may properly fulfil its function of a circumferential gripping element for the capillary.

Between the hollow cylindrical extension section and the tapering back section, the connection section may be located which increases its diameter from the hollow cylindrical extension section towards the mostly extended part of the tapering back section, thereby forming a hill-like structure together with the tapering back section. Alternatively, an abrupt transition between the hollow cylindrical extension section and the tapering back section is possible (i.e. the connection section may be omitted).

In an embodiment, the ferrule chuck, particularly a tapering back section of the ferrule chuck, has a longitudinal slit, particularly has a plurality of longitudinal slits distributed equally around a circumference of the ferrule chuck. In this context, the term "longitudinal" or axial again refers to the extension direction of the capillary. In other words, the slits may be oriented in parallel to the extension of the capillary. The length of the slit(s) may define the length of the spring like portion of the ferrule chuck.

In a preferred embodiment, the tapering back section and the hollow cylindrical extension section have exactly two or exactly three longitudinal slits distributed equally around a circumference of the ferrule chuck so that a bearing (i.e. a virtual or theoretical pivoting point) for a bending of wings formed between adjacent slits is located at an interface between the hollow cylindrical extension section and the hollow cylindrical front section.

In a particularly preferred embodiment, three longitudinal slits are formed, each having a distance of 120° from the next slit. By taking this measure, three spring-like wings are formed in the hollow cylindrical extension section and the tapering back section, each wing being formed by a region between two adjacent slits. It has been recognized that, upon using three spring-like elements formed between three slits (combined with a well-balanced thickness of the hollow cylindrical extension section), a bending line of the corresponding spring is located very close to the capillary. This, in turn, results in a large contacting area between ferrule chuck and capillary, thereby ensuring a proper embossing of the capillary and hence a proper grip. In other words, the center of area of the theoretically bearing formed at an interface between hollow cylindrical extension section and hollow cylindrical front section is located very close to the capillary when forming exactly three wings and valid wall thickness of the hollow cylindrical extension section (as thin as possible, however without a loss of elastic properties of the wings; this may depend on the hardness of the used material). The more slits are used exceeding the number of three, the stronger becomes the deviation from a snugly alignment of the wings onto the capillary. Reasonable results can still be achieved when forming two wings by providing two slits. However, when further reducing the number of slits to one, the structure becomes quite stiff, contravening a proper alignment of the ferrule chuck towards the capillary.

Still referring to the previously described embodiment, the slit or slits may end before the hollow cylindrical front section. In this case, the hollow cylindrical front section may or may not be thickened compared to the hollow cylindrical extension section. Alternatively, the slit or slits may extend into the hollow cylindrical front section (which may be achievable with a very simple processing technique). In the latter case, the portion of the slit in the hollow cylindrical front section may be a recess such as a hole (like a through hole) so that the hollow cylindrical front section does not form part to a bendable wing limited between adjacent slits and does not contribute to the spring-like property of such a bendable wing.

In an embodiment, spring-like wings are formed between each pair of adjacent slits. A bending axis of at least one of the spring-like wings has a distance to an outer surface of the capillary of at the maximum approximately ±0.5 mm (wherein the "+" refers to a position of the theoretical or virtual bending axis outside of the capillary, and the "−" refers to a position of the theoretical or virtual bending axis inside of the capillary), particularly of at the maximum approximately ±0.1 mm. Preferably, the bending axis of at least one of the spring-like wings is a tangent to the outer surface of the capillary. The closer the bending axis (or bending line or bending trajectory) is located with respect to the cylindrical exterior surface of the capillary, the better is the contact area with the microprotrusions aligned to the exterior surface of the capillary, i.e. the better is the form closure based grip. In an embodiment, the bending line is located quite close to the perimeter of the capillary, so that, contrary to prior approaches, no deep extended grooves or deep macroscopic markings are formed in the capillary.

In an embodiment, the ferrule chuck and the ferrule are configured to abut directly against one another when the fitting is in an assembled state, for instance when being accommodated within the housing. Hence, there may be a direct contact between ferrule chuck and ferrule without any further member in between, Alternatively, it is possible that one or more intermediate pieces may be between the ferrule chuck and the ferrule (such as a gripping disk or a spring, for instance a spring disk or a washer).

In an embodiment, the ferrule has a tapering, particularly a conically tapering, front section, wherein the tapering front section extends at least partially beyond the housing. Hence, a rear part of the tapering front section is accommodated within the housing, whereas a front part protrudes over the housing so as to be insertable into a corresponding recess of a counter piece, thereby providing a sealing connection to the counter piece.

In an embodiment, the ferrule has an annular, particularly a flat annular, back surface, wherein the annular back surface abuts against an annular front surface of the ferrule chuck. The back surface of the ferrule may have the same shape and dimension as the front surface of the ferrule chuck, thereby providing a proper force transmission.

In an embodiment, the ferrule has a hollow cylindrical back section ending at the annular back surface. Again, also the cylindrical back section of the ferrule may act as a support without being bent upon applying connection forces.

In an embodiment, the ferrule has a hollow cylindrical extension section arranged between the hollow cylindrical back section and the tapering front section, wherein the hollow cylindrical extension section may have a smaller wall thickness than the hollow cylindrical back section. However, the thickness of the cylindrical extension section of the ferrule may be larger, for instance at least twice or at least three times larger, than the thickness of the hollow cylindrical extension section of the ferrule chuck. The hollow cylindrical extension section of the ferrule chuck may have an integrated spring for proper alignment to the ferrule.

In an embodiment, the housing, the ferrule, and the ferrule chuck form a male piece of the fitting, the male piece further having a first joint element at an exterior surface of the housing. The fitting may further comprise a female piece having a recess configured for accommodating at least part of the ferrule and the capillary and having a second joint element configured to be joinable to the first joint element. This female piece may hence receive at least a part of the ferrule and at least a part of the housing of the fitting. For instance, the joint elements may provide for a screwing connection and may hence be an internal thread and a corresponding external thread. However, the joint elements may also be configured in another way such as to form a snap-in connection or a bayonet connection.

In an embodiment, the ferrule comprises an elastic material, particularly a polymer material or a metal. The ferrule chuck may comprise an elastic material such as steel (having spring properties over a section thereof). The ferrule chuck may be made of a material having a hardness exceeding a hardness of a material from which the capillary is made. If this condition is fulfilled, it is also possible that the ferrule chuck is made from another material than a metal, for instance a plastic material or a ceramic material.

In an embodiment, the fitting comprising the capillary. Therefore, the capillary may form part of the fitting. The capillary may be slidable relative to the ferrule and/or the ferrule chuck when the fitting is not connected to the other component and may be immobilized when the fitting is connected to the other component.

In an embodiment, the capillary comprises a metal, stainless steel, titan, a plastic, a polymer, glass and/or quartz. The capillary may have a lumen having a diameter of less than 0.8 mm, particularly of less than 0.2 mm. Other materials and dimensions are however possible as well.

In an embodiment, the microstructure is formed by spark-eroding material of the ferrule chuck. Electric discharge machining (EDM), also referred to as spark machining, spark eroding, burning, die sinking or wire erosion, is a manufacturing process whereby a desired shape is obtained using electrical discharges (sparks). Material is removed from the workpiece by a series of rapidly recurring current discharges between two electrodes, separated by dielectric liquid and subject to an electric voltage. It has turned out that spark-eroding is a powerful tool of forming the microstructures in a cheap and simple manner. However, other manufacturing processes such as laser processing, sputtering, lithography and etching methods are possible as well. It is also possible to form the microprotrusions by deposition of material on the surface of the ferrule chuck.

Next, further representative embodiments of the fluidic device will be explained. However, these embodiments also apply to the fitting and to the method.

Fluidic devices according to representative embodiments may be particularly suitable for use as fluidic connection pieces for connecting parts of a fluidic instrument such as a liquid chromatographic system or the like. For example, columns, fractioners, detectors, etc., of a liquid chromatography apparatus may be connected to a capillary by such fittings.

A component to be coupled to the capillary by the fitting may be a fluidic sample processing element such as a separation column. Such a separation column may include material which may also be denoted as a stationary phase which may be any material which allows an adjustable degree of interaction with a sample so as to be capable of separating different components of such a sample. The separating material may be a liquid chromatography column filling material or packing material comprising at least one of the group consisting of polystyrene, zeolite, polyvinylalcohol, polytetrafluorethylene, glass, polymeric powder, silicon dioxide, and silica gel, or any of above with chemically modified (coated, capped etc) surface. However, any packing material can be used which has material properties allowing an analyte passing through this material to be separated into different components, for instance due to different kinds of interactions or affinities between the packing material and fractions of the analyte.

At least a part of the processing element may be filled with such a fluid separating material, wherein the fluid separating material may comprise beads having a size in the range of essentially 1 µm to essentially 50 µm. Thus, these beads may be small particles which may be filled inside the separation section of the microfluidic device. The beads may have pores having a size in the range of essentially 0.01 µm to essentially 0.2 µm. The fluidic sample may be passed through the pores, wherein an interaction may occur between the fluidic sample and the pores.

The fluidic device may be configured as a fluid separation system for separating components of the sample. When a mobile phase including a fluidic sample passes through the fluidic device, for instance with a high pressure, the interaction between a filling of the column and the fluidic sample may allow for separating different components of the sample, as performed in a liquid chromatography device.

However, the fluidic device may also be configured as a fluid purification system for purifying the fluidic sample. By spatially separating different fractions of the fluidic sample, a multi-component sample may be purified, for instance a protein solution. When a protein solution has been prepared in a biochemical lab, it may still comprise a plurality of components. If, for instance, only a single protein of this multi-component liquid is of interest, the sample may be forced to pass the columns. Due to the different interaction of the different protein fractions with the filling of the column (for instance using a gel electrophoresis device or a liquid chromatography device), the different samples may be distinguished, and one sample or band of material may be selectively isolated as a purified sample.

The fluidic device may be configured to analyze at least one physical, chemical and/or biological parameter of at least one component of the mobile phase. The term "physical parameter" may particularly denote a size or a temperature of the fluid. The term "chemical parameter" may particularly denote a concentration of a fraction of the analyte, an affinity parameter, or the like. The term "biological parameter" may particularly denote a concentration of a protein, a gene or the like in a biochemical solution, a biological activity of a component, etc.

The fluidic device may be implemented in different technical environments, like a sensor device, a device for chemical, biological and/or pharmaceutical analysis, a capillary electrophoresis device, a liquid chromatography device, a gas chromatography device, or a mass spectroscopy device. Particularly, the fluidic device may be a High Performance Liquid device (HPLC) device by which different fractions of an analyte may be separated, examined and analyzed.

The fluidic device may be configured to conduct the mobile phase through the system with a high pressure, particularly of at least 1200 bar, more particularly of at least 2000 bar.

The fluidic device may be configured as a microfluidic device. The term "microfluidic device" may particularly denote a fluidic device as described herein which allows to convey fluid through microchannels having a dimension in the order of magnitude of less than 800 µm, particularly less than 200 µm, more particularly less than 100 µm or less than 50 µm or less.

BRIEF DESCRIPTION OF DRAWINGS

The illustrative embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

The illustration in the drawing is schematically.

Before the figures will be described in further detail, some considerations underlying the present invention will be summarized. In an embodiment, a ferrule chuck with a surface micro-grip as a generic capillary connection is provided. According to prior solutions, ferrules for capillary connections are either made of polymers or are made of stainless steel. Polymeric ferrules grip due to frictional force and stainless steel ferrules bite with low surface contact causing form closure onto the stainless steel capillaries or support only frictional force like polymeric ferrules. There is low robustness and weak performance especially with system pressure above 400 bar. Further limitations occur with higher environmental temperature (up to 100° C.) and hard drawn stainless steel capillaries. A ferrule chuck of an embodiment of the invention has a surface micro grip made of stainless steel with a hardness of at least 44 HRC and covers applications to all stainless steel capillaries available, up to 300° C. or more and system pressure up to 2000 bar or more. First experiments have shown that the micro grip extends the frictional grip by far without disruptive marks to the stainless steel capillary. The special material used for the chuck helps to preserve the micro structure and stands for very long time of use. The geometry of the chuck is designed to provide a relatively large area of contact to the capillary when clamped. The manufacturing process is arranged that the final surface trimming along the area of contact to the capillary is spark-eroded to a microgrip without burrs at edges and slots.

DETAILED DESCRIPTION

In the following detailed description, for purposes of explanation and not limitation, illustrative embodiments disclosing specific details are set forth in order to provide a thorough understanding of embodiments according to the present teachings. However, it will be apparent to one having had the benefit of the present disclosure that other embodiments according to the present teachings that depart from the specific details disclosed herein remain within the scope of the appended claims. Moreover, descriptions of well-known devices and methods may be omitted so as not to obscure the description of the example embodiments. Such methods and devices are within the scope of the present teachings.

Generally, it is understood that the drawings and the various elements depicted therein are not drawn to scale. Further, relative terms, such as "above," "below," "top," "bottom," "upper," "lower," "left," "right," "vertical" and "horizontal," are used to describe the various elements' relationships to one another, as illustrated in the accompanying drawings. It is understood that these relative terms are intended to encompass different orientations of the device and/or elements in addition to the orientation depicted in the drawings. For example, if the device were inverted with respect to the view in the drawings, an element described as "above" another element, for example, would now be "below" that element. Likewise, if the device were rotated 90 degrees with respect to the view in the drawings, an element described as "vertical," for example, would now be "horizontal."

In the following, referring to FIG. 1, a fitting 100 for coupling a capillary 102 to a connected fluidic conduit 188 of another fluidic component such as a liquid chromatography column (not shown in FIG. 1) of a liquid chromatography device according to an representative embodiment of the invention will be explained. FIG. 2 shows an enlarged portion of a part of the fitting 100.

Figure 1:
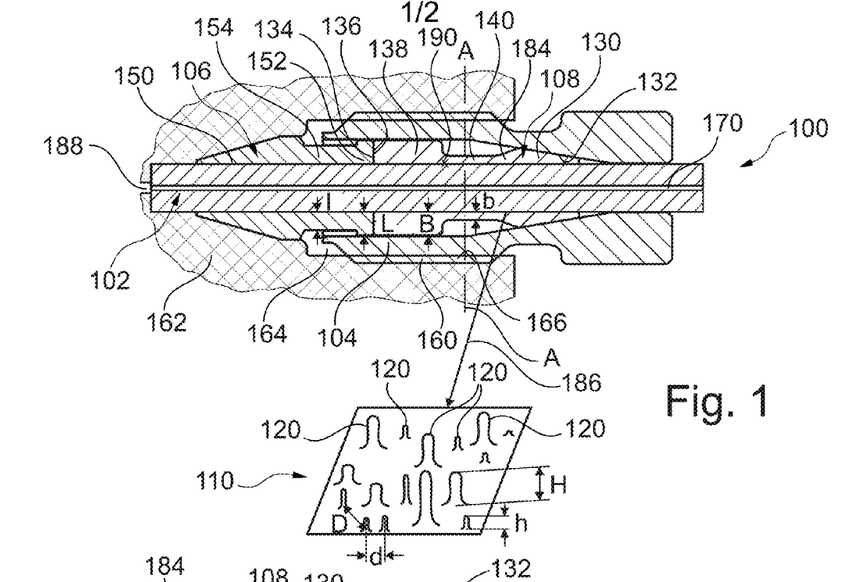
FIG. 1 illustrates a cross-sectional view of a fitting according to an representative embodiment.
Figure 2:
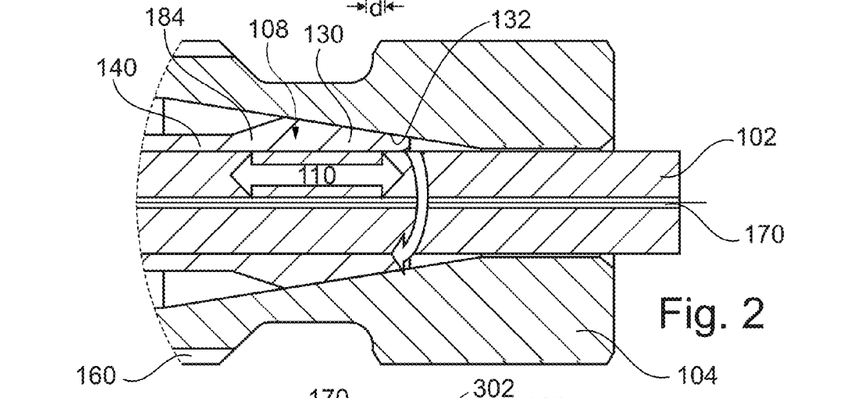
FIG. 2 illustrates a detail of the fitting of FIG. 1.

Fitting 100 shown in FIG. 1 has a male piece predominantly formed by components 102, 104, 106 and 108. Furthermore, the fitting 100 has a correspondingly shaped female piece, constituted by a recessed housing 162. The fitting 100 is capable of providing a fluidic connection between a lumen 170 within the capillary 102 on the one hand and the connected fluidic conduit 188 on the other hand. The sealing connection is fluid tight at a pressure of 2000 bar of a fluid (such as a liquid) flowing through the lumen 170 and subsequently through the fluidic conduit 188.

The fitting 100 comprises a ferrule 106 which is configured for enclosing a front part of the capillary 102 and for contributing to a fluidic sealing between the fitting 100 and the other component (connected to or containing the housing 162). More precisely, the sealing between the fitting 100 and the connected component is achieved by the form closure between an exterior surface of the ferrule 106 and the corresponding inner surface of the housing 162. Since the ferrule 106 is made of a plastic material such as PEEK, it will be pressed sealingly against the corresponding surface of the recessed housing 162 upon forming a screwing connection between an external thread 160 of housing 104 of the fitting 100 on the one hand and an internal thread 166 of the further housing 164. This will press the ferrule 106, which is made of the slightly deformable polymer material, against a corresponding surface of the metallic housing 162, therefore providing for a fluid-tight connection. In view of the chosen geometry and the resulting fluid-tight connection, carryover of historic sample material is avoided while at the same time providing for a small dead volume. The capillary 102 will further be pressed forwardly, i.e. towards the left hand side of FIG. 1, so as to provide for a sealing connection with the connected sealing conduit 188.

Apart from the ferrule 106, the fitting 100 comprises a ferrule chuck 108 which is configured for enclosing a back part of the capillary 102, as shown in FIG. 1. Referring to FIG. 1, the term "front" refers to a connection position between capillary 102 and fluidic conduit 188, whereas the term "back" refers to an opposing section of the capillary 102 located remotely from the fluidic interface between components 102 and 188 within the housing 104.

The ferrule chuck 108 has, at a lateral end of the hollow cylindrical front section 138, a flat annular front surface 134 abutting against a correspondingly shaped and dimensioned annular back surface 136 of the ferrule 106.

The capillary 102 is slidable relative to the ferrule 106 and relative to the ferrule chuck 108 and is made, in the present embodiment, of stainless steel. The lumen 170 of the capillary 102 has an internal diameter of 0.17 mm.

The housing 104 also forms part of the fitting 100 and is configured for accommodating the ferrule chuck 108 as well as a part or subsection of the ferrule 106. The internal shaping of the housing 104 is configured so that it will push the ferrule chuck 108 against the ferrule 106 when the fitting 100 is tightened with or connected to the other component. At the same time, the formation of the screwing connection between threads 160 and 166 will also generate a circumferential gripping form fit between a microstructure 110 of the ferrule chuck 108 and an inverse arrangement of microindentations on the capillary 102. To generate the circumferential gripping form fit, a circumferential force is applied from the housing 104 via the ferrule chuck 108 towards the capillary 102. Hence, the housing 104 is also configured for circumferentially pressing the ferrule chuck 108 against the capillary 102.

FIG. 1 furthermore shows a detail 186 of the constitution of an interior cylindrical surface of the ferrule chuck 108. As can be taken from detail 186, this interior cylindrical surface is provided with microstructure 110. The microstructure 110 is formed as a large plurality of microprotrusions 120 (for instance a number of 10000) which extend over the inner surface of the ferrule chuck 108. The various microprotrusions 120 of the microstructure 110 are in gripping form fit with the enclosed back part of the capillary 102 over a cylindrical contact area with the length of 2 mm and over the circumferential extension (interrupted by slits) between the ferrule chuck 108 and the capillary 102. When the fitting 100 is tightened or fastened to the other component by joining the screwing connection between the threads 160 and 166, the microstructure 110 (of microprotrusions 120) protrudes or embosses into a counter surface of the capillary 102 thereby forming an inverse microstructure (of microindentations) in the counter surface of the capillary 102. The result is a form closure or form fit between the ferrule chuck 108 and the capillary 102 thereby guaranteeing a proper grip.

The dimensions of the irregularly arranged microprotrusions 120 may be for instance between 2 μm and 20 μm. As can be taken from the detail 186 in FIG. 1, adjacent microprotrusions 120 have different dimensions (for instance differ regarding height, compare h and H) and/or differ regarding a distance between adjacent pairs of microprotrusions 120 (compare D, d). Since the microprotrusions 120 are formed with a random distribution, i.e. without a regular pattern or ordering scheme on the support surface of the ferrule chuck 108, the exterior cylindrical surface of the ferrule chuck 108 with the microprotrusions 120 will emboss an irregular pattern on the capillary 102. The irregularity of these patterns on the ferrule chuck 108 and on the capillary 102 do advantageously, upon reusing the capillary with the same or another fitting, not result in a predefined gripping position between capillary and fitting. In contrast to this, a gripping position and consequently a relative orientation between the ferrule chuck 108 and the capillary 102 remains freely selectable by a user even when reusing a capillary 102 with already embossed microindentations. At the same time, the microprotrusions 120 have the effect that they significantly increase the gripping form fit applied to the capillary 102, thereby being capable of providing gripping forces suitable for 2000 bar applications, such as required in modern liquid chromatography.

The ferrule chuck 108 is made of stainless steel having a Rockwell hardness of 44 HRC. The ferrule chuck 108 has four portions. As shown on the right hand side of FIG. 1, the ferrule chuck 108 has a conically tapering back section 130 which abuts against a corresponding tapering surface 132 of the housing 104. The tapering back section 130 is configured for generating the gripping form fit by transferring a force (directed circumferentially inwardly) from the housing 104 to the capillary 102, thereby allowing to circumferentially grip the capillary 102. This gripping is promoted and supported by the microstructure 110 which is formed on an inner cylindrical surface of the tapering back section 130. Directly connected to the tapering back section 130, starting from a local maximum of the hill-like right hand side portion of the ferrule chuck 108, is a connection section 184 which connects the tapering back section 130 with a hollow cylindrical extension section 140. The hollow cylindrical extension section 140 is arranged between a more bulky hollow cylindrical front section 138 and the above described tapering back section 130. The hollow cylindrical extension section 140 has a very small wall thickness b which is smaller than a wall thickness B of the hollow cylindrical front section 138. Therefore, the hollow cylindrical front section 138 is connecting wings (which may form part of the same member or may be configured as separate members) of the ferrule chuck 108 to one part and acts as an undeformable support which remains basically undeformed upon providing a sealing connection between the fitting 100 and the connected component. In contrast to this, in view of the small wall thickness b of for instance 0.2 mm of the hollow cylindrical extension section 140, the latter operates as a flat spring when connecting the fitting 100 to a connected component. In view of this spring-like behavior, the hollow cylindrical extension section 140 as well as the connected tapering back section 130 and the connection section 184 are aligned against the perimeter of the capillary 102.

Although not shown in FIG. 1 and FIG. 2, but as will be described with reference to FIG. 3 below in more detail, the hollow cylindrical extension section 140 as well as the tapering back section 130 have three parallel longitudinal slits distributed with an angular distance of about 120° around a circumference of the ferrule chuck 108 and end before the hollow cylindrical front section 138. Therefore, a bearing 190 is formed at the end of these slits which serves as a virtual pivot point around which pivoting of wings formed between adjacent slits is performed. This pivoting point, as can be taken from FIG. 1, is located at an interface between the hollow cylindrical extension section 140 and the hollow cylindrical front section 138.

The ferrule 106 has a conically tapering front section 150 extending beyond the housing 104 and being accommodated within further housing 162 to provide for a fluid-tight connection between lumen 170 and fluidic conduit 188. A radially widened hollow cylindrical back section 152 of the ferrule 106 ending at the annular back surface 136 is provided as well. The hollow cylindrical back section 152 is a locally thickened portion of the ferrule 106 providing for a consequently relatively large contact area to the ferrule chuck 108. Furthermore, the ferrule 106 has a hollow cylindrical extension section 154 arranged between the hollow cylindrical back section 152 and the tapering front section 150. The hollow cylindrical extension 154 has a smaller wall thickness I then a wall thickness L of the hollow cylindrical back section 152. This profile may be designed to adjust the compression strength to the maximum allowable value and thus providing an additional axial spring loading within the ferrule 106.

As can be taken from FIG. 1, the housing 104, the ferrule 106 and the ferrule chuck 108 form a male piece of the fitting 100. This male piece further has the external thread 160 as a first joint element at an exterior surface of the housing 104. Moreover, the fitting 100 comprises the further housing 162 as a female piece having recess 164 configured for accommodating part of the ferrule 106 and the capillary 102 and having the internal thread 166 as a second joint element configured to be joinable to the external thread 160 of the housing 104.

Figure 3:
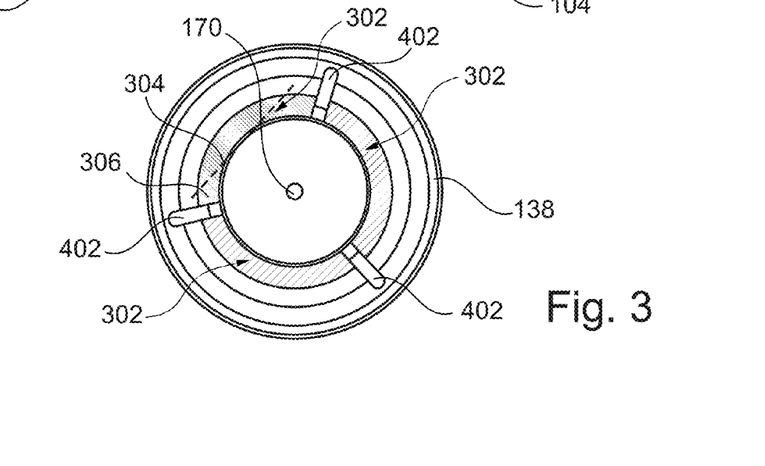
FIG. 3 illustrates a cross-sectional view only of the ferrule chuck of the fitting of FIG. 1 along an axis A-A shown in FIG. 1.

In FIG. 3, a cross-section of the ferrule chuck 108 (upright to axis and wings 302) along an axis A-A of FIG. 1 is shown. Here, the three longitudinal slits 402 are shown as well. They divide the ferrule chuck 108 into three wings 302 along the sections 140, 184 and 130, but do not extend into section 134. A bending line 304 for one of the wings 302 is plotted as well. An arcuate cross-sectional area 306 of one of the wings 302 is shown as well. It can be seen that, in view of the chosen geometry (exactly three slits, extension of the slits 402 only into sections 130, 184, 140, but radially only partly into section 138) the virtual bending line 304 is very close to an inner diameter of the respective wing 302, thereby providing for a tight and not too stiff alignment of the ferrule chuck 108 against the capillary 102.

In the shown embodiment three spring-like wings 302 are formed between each pair of adjacent slits 402. Bending axis or bending line 304 of one of the spring-like wings 302 has a distance of zero to an outer surface of the capillary 102, i.e. the bending axis 304 of the spring-like wing 302 is a tangent to the outer surface of the capillary 102. Although not drawn in FIG. 3, this applies for each of the wings 302.

In FIG. 3, reference numeral 302 relates to the pivoting wings, reference numeral 304 relates to a neutral bending axis, and reference numeral 306 relates to the cross sectional spring area at the hollow cylindrical extension section 140 of the wings 302. The three wings 302 are in 120° symmetrical partition. The cross sectional spring area 306 at the hollow cylindrical extension section 140 of the wings 302 is preferably designed to generate the neutral bending axis 304 to be a tangent line to the outer surface line of the capillary 102 or fits it close to the outer surface line of the capillary 102. Close means above or inside the nominal radius of the capillary 102 within a range of ±0.5 mm. More preferable, it is within a range of ±0.1 mm. As can be taken from FIG. 3, the centroid of the bending area and hence the neutral axis or bending axis 304 is close to the outer surface of the capillary 102.

Figure 4:
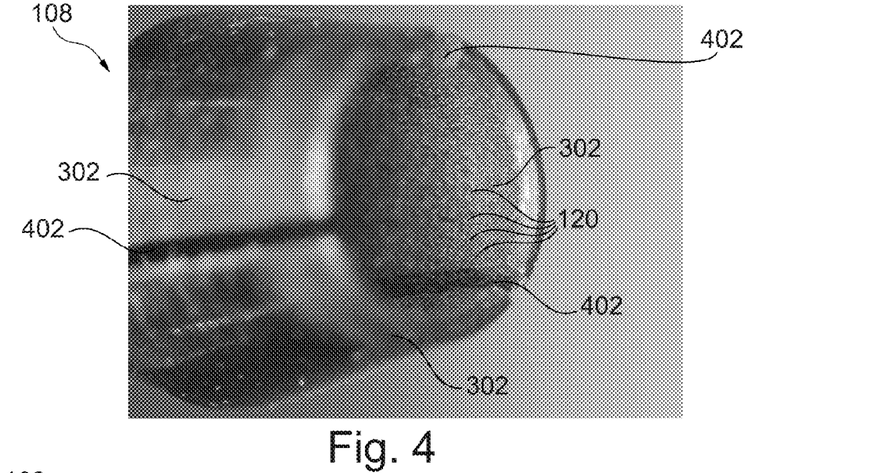
FIG. 4 and FIG. 5 are images illustrating a ferrule chuck with a surface micro-grip of a fitting according to an representative embodiment.
Figure 5:
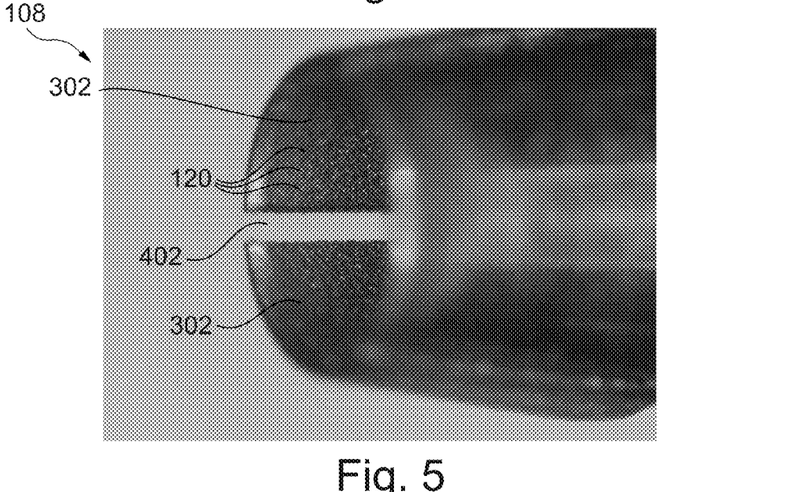

FIG. 4 and FIG. 5 show images of a ferrule chuck 108 of a fitting 100 according to an embodiment of the invention and show particularly the microprotrusions 120 at an inner surface of the ferrule chuck 108.

Figure 6:
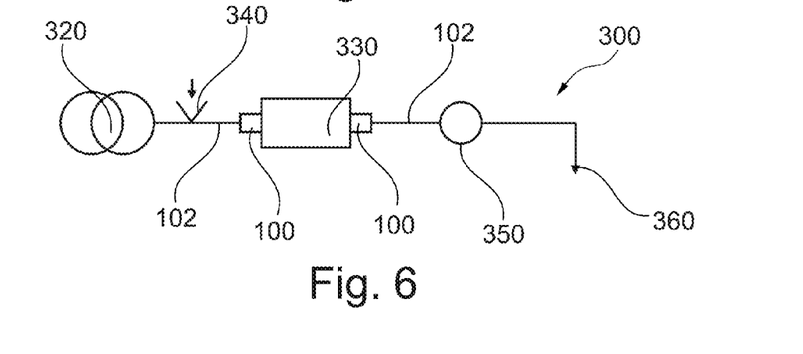
FIG. 6 illustrates a high performance liquid chromatography apparatus according to an representative embodiment.

FIG. 6 shows a HPLC (High-Performance Liquid Chromatography) system 300 for a liquid chromatography analysis of a fluidic sample according to an representative embodiment.

A pump 320 pumps a mobile phase through a chromatographic column 330 which comprises a stationary phase such as beads made of silica gel. A sample supply unit 340 is arranged between the pump 320 and the chromatographic column 330 in order to inject a fluidic sample into the mobile phase. The stationary phase of the chromatographic column 330 is provided in order to separate components of the fluidic sample which may be pumped through the chromatographic column 330 with a high pressure of, for instance, 2000 bar. A detector 350 detects the separated components of the fluidic sample. A fractioner 360 can be provided to receive the separated components of the fluidic sample, for instance to conduct them into dedicated containers or into a waste container (not shown).

As can be taken from FIG. 6, fittings 100 are used to connect an inlet and an outlet of the chromatographic column 330 to a metal capillary 102 in a liquid-sealed fashion. Additionally or alternatively, any of the other components shown in FIG. 6 may be connected to such a capillary 102 using a fitting 100.

It should be noted that the term "comprising" does not exclude other elements or features and the "a" or "an" does not exclude a plurality. Also elements described in association with different embodiments may be combined. It should also be noted that reference signs in the claims shall not be construed as limiting the scope of the claims.

The invention claimed is:

1. A fitting for coupling a capillary to another component of a fluidic device, the fitting comprising
    a ferrule configured for enclosing a front part of the capillary and for contributing to a fluidic sealing between the fitting and the other component;
    a ferrule chuck configured for enclosing a back part of the capillary;
    a housing configured for accommodating at least a part of the ferrule chuck and for pushing the ferrule chuck against the ferrule; and
    a microstructure comprising multiple microprotrusions randomly distributed on at least a part of a surface of the ferrule chuck for generating, wherein upon tightening the fitting at the other component, the microprotrusions are configured to exert a gripping interaction from the surface of the ferrule chuck and penetrating into a surface of the capillary.

2. The fitting according to claim 1, wherein the microstructure comprises multiple microprotrusions protruding from a surface of the ferrule chuck.

3. The fitting according to claim 1, wherein, for at least a part of the microprotrusions, a distance (d) between a pair of adjacent ones of the microprotrusions differs from a distance (D) between microprotrusions of other pairs of adjacent microprotrusions, which other pairs are adjacent to the pair.

4. The fitting according to claim 1, wherein at least a part of the microprotrusions are arranged over the surface of the ferrule chuck without a repeat pattern.

5. The fitting according to claim 1, wherein the microstructure is formed, on a circumferential inner surface of the ferrule chuck along which the ferrule chuck circumferentially grips the capillary.

6. The fitting according to claim 1, wherein the ferrule chuck has a tapering back section, wherein the tapering back section abuts against a tapering counter surface of the housing.

7. The fitting according to claim 6, wherein the tapering back section is configured for transmitting a gripping force from the housing to the capillary.

8. The fitting according to claim 6, wherein the microstructure is formed on a circumferential inner surface of the tapering back section.

9. The fitting according to claim 1, wherein the ferrule chuck has an annular front surface, and the annular front surface abuts against an annular back surface of the ferrule.

10. A fluidic device for processing a fluidic sample, the fluidic device comprising
    a capillary for conducting the fluidic sample;
    another component for processing the fluidic sample; and
    a fitting according to claim 1 for coupling the capillary to the other component.

11. The fluidic device according to claim 10, wherein the other component comprises a processing element configured to interact with the fluidic sample.

12. The fluidic device according to claim 11, wherein the processing element is configured for retaining the fluidic sample being a part of a mobile phase and for allowing other components of the mobile phase to pass the processing element.

13. The fluidic device according to claim 11, wherein the processing element comprises a separation column.

14. The fluidic device according to claim 11, wherein the processing element comprises a chromatographic column for separating components of the fluidic sample.

15. The fluidic device according to claim 10, configured to conduct a liquid fluidic sample through the other component.

16. The fluidic device according to claim 10, configured to conduct the fluidic sample through the other component with a high pressure.

17. The fluidic device according to claim 10, configured to conduct the fluidic sample through the other component with a pressure of at least 500 bar.

18. A fitting for coupling a capillary to another component of a fluidic device, the fitting comprising:
- a ferrule configured for enclosing a front part of the capillary and for contributing to a fluidic sealing between the fitting and the other component;
- a ferrule chuck configured for enclosing a back part of the capillary, the ferrule chuck comprising an annular front surface, the annular front surface being separated from an annular back surface of the ferrule by a gripping element configured to promote a grip between the ferrule and the ferrule chuck;
- a housing configured for accommodating at least a part of the ferrule chuck and for pushing the ferrule chuck against the ferrule; and
- a microstructure comprising multiple microprotrusions on at least a part of a surface of the ferrule chuck for generating, wherein upon tightening the fitting at the other component, the microprotrusions are configured to exert a gripping interaction from the surface of the ferrule chuck and penetrating into a surface of the capillary.

19. The fitting according to claim 18, wherein at least a part of the microprotrusions are arranged over the surface of the ferrule chuck without a repeat pattern.

20. The fitting according to claim 18, wherein the microstructure is formed, on a circumferential inner surface of the ferrule chuck along which the ferrule chuck circumferentially grips the capillary.

21. The fitting according to claim 20, wherein the tapering back section is configured for transmitting a gripping force from the housing to the capillary.

22. The fitting according to claim 20, wherein the microstructure is formed on a circumferential inner surface of the tapering back section.

23. The fitting according to claim 18, wherein the ferrule chuck has a tapering back section, wherein the tapering back section abuts against a tapering counter surface of the housing.

24. The fitting according to claim 18, wherein the ferrule chuck has an annular front surface, and the annular front surface abuts against an annular back surface of the ferrule.

25. A fluidic device for processing a fluidic sample, the fluidic device comprising
- a capillary for conducting the fluidic sample;
- another component for processing the fluidic sample; and
- a fitting according to claim 18 for coupling the capillary to the other component.

26. The fluidic device according to claim 25, wherein the processing element is configured for retaining the fluidic sample being a part of a mobile phase and for allowing other components of the mobile phase to pass the processing element.

27. The fluidic device according to claim 25, wherein the processing element comprises a separation column.

28. The fluidic device according to claim 25, wherein the processing element comprises a chromatographic column for separating components of the fluidic sample.

29. The fluidic device according to claim 24, wherein the other component comprises a processing element configured to interact with the fluidic sample.

30. The fluidic device according to claim 24, configured to conduct a liquid fluidic sample through the other component.

31. The fluidic device according to claim 24, configured to conduct the fluidic sample through the other component with a high pressure.

32. The fluidic device according to claim 24, configured to conduct the fluidic sample through the other component with a pressure of at least 500 bar.

33. A fitting for coupling a capillary to another component of a fluidic device, the fitting comprising:
- a ferrule configured for enclosing a front part of the capillary and for contributing to a fluidic sealing between the fitting and the other component;
- a ferrule chuck configured for enclosing a back part of the capillary, the ferrule chuck comprising an annular front surface, the annular front surface being separated from an annular back surface of the ferrule by a gripping element configured to promote a grip between the ferrule and the ferrule chuck;
- a housing configured for accommodating at least a part of the ferrule chuck and for pushing the ferrule chuck against the ferrule; and
- a microstructure comprising multiple microprotrusions on at least a part of a surface of the ferrule chuck for generating, wherein at least a part of the microprotrusions has a dimension (h), which differs from a corresponding dimension (H) of at least a part of adjacent ones of the microprotrusions.

34. A fitting for coupling a capillary to another component of a fluidic device, the fitting comprising:
- a ferrule configured for enclosing a front part of the capillary and for contributing to a fluidic sealing between the fitting and the other component;
- a ferrule chuck configured for enclosing a back part of the capillary, the ferrule chuck comprising an annular front surface, the annular front surface being separated from an annular back surface of the ferrule by a gripping element configured to promote a grip between the ferrule and the ferrule chuck;
- a housing configured for accommodating at least a part of the ferrule chuck and for pushing the ferrule chuck against the ferrule; and
- a microstructure comprising multiple microprotrusions on at least a part of a surface of the ferrule chuck for generating, wherein, for at least a part of the microprotrusions, a distance (d) between a pair of adjacent ones of the microprotrusions differs from a distance (D) between microprotrusions of other pairs of adjacent microprotrusions, which other pairs are adjacent to the pair.

* * * * *